(12) United States Patent
Schwarz

(10) Patent No.: US 7,264,803 B2
(45) Date of Patent: Sep. 4, 2007

(54) METHODS AND PHARMACEUTICAL FORMULATIONS FOR THE TREATMENT OF PULMONARY HYPERTENSION

(75) Inventor: Margaret A. Schwarz, La Canada-Flintridge, CA (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 283 days.

(21) Appl. No.: 10/274,788

(22) Filed: Oct. 21, 2002

(65) Prior Publication Data

US 2003/0039652 A1     Feb. 27, 2003

Related U.S. Application Data

(63) Continuation of application No. 09/738,685, filed on Dec. 15, 2000, now abandoned.

(60) Provisional application No. 60/177,008, filed on Jan. 19, 2000, provisional application No. 60/197,492, filed on Apr. 17, 2000.

(51) Int. Cl.
*A61K 39/00* (2006.01)
*A61K 39/395* (2006.01)

(52) U.S. Cl. ............... 424/130.1; 424/133.1; 424/141.1; 424/145.1

(58) Field of Classification Search ............ 424/130.1, 424/133.1, 141.1, 142.1, 145.1; 530/387.1
See application file for complete search history.

(56) References Cited

U.S. PATENT DOCUMENTS 5,641,867 A      6/1997   Stern et al.

FOREIGN PATENT DOCUMENTS

| WO | WO95/09180 | * | 4/1995 |
|----|------------|---|--------|
| WO | WO 00/29620 |   | 5/2000 |
| WO | WO 01/47518 |   | 7/2001 |

OTHER PUBLICATIONS

Stryer et al, in Biochemistry, Third edition, W H Freeman Company, New York, pp. 31-33, 1998.*
Gallie et al, Eur Respir J 20: 1037-149, 2002.*
Abstract, Schwarz, Margaret, et al., Emap ii: a modulator of neovascularization in the developing lung, *APStracts 5:0339L* (1998).
Gaine, Sean P., et al., Primary pulmonary hypertension, *Lancet*, vol. 352, pp. 719-725 (1998).
Bennett et al., *Biochemical Pharmacology*, vol. 55, pp. 9-19 (1998).
Kao, Janet, et al.; Characterization of a Novel Tumor-derived Cytokine, *The Journal of Biological Chemistry*, vol. 269, No. 40, pp. 25106-25119 (Oct. 7, 1994).

* cited by examiner

*Primary Examiner*—Christina Chan
*Assistant Examiner*—Phuong Huynh
(74) *Attorney, Agent, or Firm*—Myers Bigel Sibley & Sajovec

(57) ABSTRACT

A method of treating pulmonary hypertension in a subject in need of such treatment comprises inhibiting EMAP II activity in the subject by an amount effective to treat the pulmonary hypertension in the subject (e.g., in the lungs and more particularly in the pulmonary vasculature). Pharmaceutical formulations useful for carrying out such methods (e.g., an antibody that specifically binds to EMAP II in a pharmaceutically acceptable carrier) and screening techniques useful for identifying additional compounds that can be used for carrying out such methods are also disclosed.

5 Claims, No Drawings

SEQUENCE LISTING

<160> NUMBER OF SEQ ID NOS: 4

<210> SEQ ID NO 1
<211> LENGTH: 1086
<212> TYPE: DNA
<213> ORGANISM: Mus musculus
<220> FEATURE:
<221> NAME/KEY: CDS
<222> LOCATION: (64)..(993)

<400> SEQUENCE: 1

```
gaggctgctc aagagctgcg gttgggtcac cgcttcatgt ttctctgccg attctgggga        60 aag atg gca acg aat gat gct gtt ctg aag agg ctg gag cag aag ggt       108
    Met Ala Thr Asn Asp Ala Val Leu Lys Arg Leu Glu Gln Lys Gly
    1               5                  10                  15 gca gag gcg gat cag atc atc gaa tat ctc aag cag cag gtt gct ctt       156
Ala Glu Ala Asp Gln Ile Ile Glu Tyr Leu Lys Gln Gln Val Ala Leu
                20                  25                  30 ctt aag gag aaa gca att ttg cag gca aca atg aga gaa gaa aag aaa       204
Leu Lys Glu Lys Ala Ile Leu Gln Ala Thr Met Arg Glu Glu Lys Lys
            35                  40                  45 ctt cga gtt gaa aat gct aaa ctg aaa aaa gaa ata gaa gag cta aag       252
Leu Arg Val Glu Asn Ala Lys Leu Lys Lys Glu Ile Glu Glu Leu Lys
        50                  55                  60 caa gag ctg att ctg gca gaa att cat aac gga gtg gag caa gtg cgt       300
Gln Glu Leu Ile Leu Ala Glu Ile His Asn Gly Val Glu Gln Val Arg
    65                  70                  75 gtt cga ttg agt act cca ctg cag acg aac tgt act gct tct gaa agt       348
Val Arg Leu Ser Thr Pro Leu Gln Thr Asn Cys Thr Ala Ser Glu Ser
80                  85                  90                  95
```

| | | |
|---|---|---|
| gtg gtg cag tct cca tca gta gca acc acc gcc tct cct gct aca aaa<br>Val Val Gln Ser Pro Ser Val Ala Thr Thr Ala Ser Pro Ala Thr Lys<br>100                       105                     110 | 396 |
| gag cag atc aaa gcg gga gaa gaa aag aag gtg aaa gag aag act gaa<br>Glu Gln Ile Lys Ala Gly Glu Glu Lys Lys Val Lys Glu Lys Thr Glu<br>            115                     120                     125 | 444 |
| aag aaa gga gag aaa aag gag aag cag cag tcg gca gca gca agt act<br>Lys Lys Gly Glu Lys Lys Glu Lys Gln Gln Ser Ala Ala Ala Ser Thr<br>                130                     135                     140 | 492 |
| gac tcc aag cct atc gac gca tcg cgt ctg gat ctt cga att ggt tgt<br>Asp Ser Lys Pro Ile Asp Ala Ser Arg Leu Asp Leu Arg Ile Gly Cys<br>145                     150                     155 | 540 |
| att gtt act gcc aag aag cac cct gat gca gat tca ctg tat gtg gag<br>Ile Val Thr Ala Lys Lys His Pro Asp Ala Asp Ser Leu Tyr Val Glu<br>160                     165                     170                     175 | 588 |
| gaa gta gat gtg gga gaa gca gcc ccg cgc acg gtc gtc agc ggg ctg<br>Glu Val Asp Val Gly Glu Ala Ala Pro Arg Thr Val Val Ser Gly Leu<br>                     180                             185                   190 | 636 |
| gtg aat cat gtt cct cta gaa cag atg caa aat cgt atg gtg gtt tta<br>Val Asn His Val Pro Leu Glu Gln Met Gln Asn Arg Met Val Val Leu<br>                195                     200                     205 | 684 |
| ctc tgt aat ctg aag cct gca aag atg cgg gga gtt ctg tct caa gcc<br>Leu Cys Asn Leu Lys Pro Ala Lys Met Arg Gly Val Leu Ser Gln Ala<br>            210                     215                     220 | 732 |
| atg gtg atg tgt gcc agt tca cca gag aaa gtg gag att ctg gcc cct<br>Met Val Met Cys Ala Ser Ser Pro Glu Lys Val Glu Ile Leu Ala Pro<br>225                     230                     235 | 780 |
| ccc aac ggg tcc gtt cct ggg gac aga att act ttt gat gct ttt cct<br>Pro Asn Gly Ser Val Pro Gly Asp Arg Ile Thr Phe Asp Ala Phe Pro<br>240                     245                     250                     255 | 828 |
| gga gag cct gac aag gag cta aac cct aag aag aag atc tgg gag cag<br>Gly Glu Pro Asp Lys Glu Leu Asn Pro Lys Lys Lys Ile Trp Glu Gln<br>                     260                             265                   270 | 876 |
| atc cag cct gac ctg cac acc aat gct gag tgt gtg gcc aca tac aaa<br>Ile Gln Pro Asp Leu His Thr Asn Ala Glu Cys Val Ala Thr Tyr Lys<br>                     275                     280                     285 | 924 |
| gga gct ccc ttt gag gtg aag ggg aag gga gtt tgc aga gcc caa acc<br>Gly Ala Pro Phe Glu Val Lys Gly Lys Gly Val Cys Arg Ala Gln Thr<br>            290                     295                     300 | 972 |
| atg gcc aat agt gga att aaa taagtgctct gtaactgaaa gacattggcg<br>Met Ala Asn Ser Gly Ile Lys<br>305                     310 | 1023 |
| aaaacttaat aacaataaag agaagtgtgt ttatcactta catataaaaa aaaaaaaaaa | 1083 |
| aaa | 1086 |

<210> SEQ ID NO 2
<211> LENGTH: 310
<212> TYPE: PRT
<213> ORGANISM: Mus musculus

<400> SEQUENCE: 2

Met Ala Thr Asn Asp Ala Val Leu Lys Arg Leu Glu Gln Lys Gly Ala
1               5                   10                   15

Glu Ala Asp Gln Ile Ile Glu Tyr Leu Lys Gln Gln Val Ala Leu Leu
               20                   25                   30

Lys Glu Lys Ala Ile Leu Gln Ala Thr Met Arg Glu Glu Lys Lys Leu
         35                   40                   45

Arg Val Glu Asn Ala Lys Leu Lys Lys Glu Ile Glu Glu Leu Lys Gln
 50                  55                   60

```
Glu Leu Ile Leu Ala Glu Ile His Asn Gly Val Gln Val Arg Val
 65                  70                  75                  80

Arg Leu Ser Thr Pro Leu Gln Thr Asn Cys Thr Ala Ser Glu Ser Val
                 85                  90                  95

Val Gln Ser Pro Ser Val Ala Thr Thr Ala Ser Pro Ala Thr Lys Glu
                100                 105                 110

Gln Ile Lys Ala Gly Glu Glu Lys Lys Val Lys Glu Lys Thr Glu Lys
                115                 120                 125

Lys Gly Glu Lys Lys Glu Lys Gln Gln Ser Ala Ala Ala Ser Thr Asp
130                 135                 140

Ser Lys Pro Ile Asp Ala Ser Arg Leu Asp Leu Arg Ile Gly Cys Ile
145                 150                 155                 160

Val Thr Ala Lys Lys His Pro Asp Ala Asp Ser Leu Tyr Val Glu Glu
                165                 170                 175

Val Asp Val Gly Glu Ala Ala Pro Arg Thr Val Val Ser Gly Leu Val
                180                 185                 190

Asn His Val Pro Leu Glu Gln Met Gln Asn Arg Met Val Val Leu Leu
            195                 200                 205

Cys Asn Leu Lys Pro Ala Lys Met Arg Gly Val Leu Ser Gln Ala Met
210                 215                 220

Val Met Cys Ala Ser Ser Pro Glu Lys Val Glu Ile Leu Ala Pro Pro
225                 230                 235                 240

Asn Gly Ser Val Pro Gly Asp Arg Ile Thr Phe Asp Ala Phe Pro Gly
                245                 250                 255

Glu Pro Asp Lys Glu Leu Asn Pro Lys Lys Ile Trp Glu Gln Ile
                260                 265                 270

Gln Pro Asp Leu His Thr Asn Ala Glu Cys Val Ala Thr Tyr Lys Gly
                275                 280                 285

Ala Pro Phe Glu Val Lys Gly Lys Gly Val Cys Arg Ala Gln Thr Met
290                 295                 300

Ala Asn Ser Gly Ile Lys
305                 310

<210> SEQ ID NO 3
<211> LENGTH: 312
<212> TYPE: PRT
<213> ORGANISM: Homo sapiens

<400> SEQUENCE: 3

Met Ala Asn Asn Asp Ala Val Leu Lys Arg Leu Glu Gln Lys Gly Ala
  1               5                  10                  15

Glu Ala Asp Gln Ile Ile Glu Tyr Leu Lys Gln Gln Val Ser Leu Leu
                 20                  25                  30

Lys Glu Lys Ala Ile Leu Gln Ala Thr Leu Arg Glu Glu Lys Lys Leu
                 35                  40                  45

Arg Val Glu Asn Ala Lys Leu Lys Lys Glu Ile Glu Glu Leu Lys Gln
             50                  55                  60

Glu Leu Ile Gln Ala Glu Ile Gln Asn Gly Val Lys Gln Ile Pro Phe
 65                  70                  75                  80

Pro Ser Gly Thr Pro Leu His Ala Asn Ser Met Val Ser Glu Asn Val
                 85                  90                  95

Ile Gln Ser Thr Ala Val Thr Val Ser Ser Gly Thr Lys Glu Gln
                100                 105                 110

Ile Lys Gly Gly Thr Gly Asp Glu Lys Lys Ala Lys Glu Lys Ile Glu
                115                 120                 125
```

-continued

```
Lys Lys Gly Glu Lys Lys Glu Lys Lys Gln Gln Ser Ile Ala Gly Ser
    130             135             140
Ala Asp Ser Lys Pro Ile Asp Val Ser Arg Leu Asp Leu Arg Ile Gly
145             150             155             160
Cys Ile Ile Thr Ala Arg Lys His Pro Asp Ala Asp Ser Leu Tyr Val
            165             170             175
Glu Glu Val Asp Val Gly Glu Ile Ala Pro Arg Thr Val Val Ser Gly
            180             185             190
Leu Val Asn His Val Pro Leu Glu Gln Met Gln Asn Arg Met Val Ile
            195             200             205
Leu Leu Cys Asn Leu Lys Pro Ala Lys Met Arg Gly Val Leu Ser Gln
    210             215             220
Ala Met Val Met Cys Ala Ser Ser Pro Glu Lys Ile Glu Ile Leu Ala
225             230             235             240
Pro Pro Asn Gly Ser Val Pro Gly Asp Arg Ile Thr Phe Asp Ala Phe
            245             250             255
Pro Gly Glu Pro Asp Lys Glu Leu Asn Pro Lys Lys Lys Ile Trp Glu
            260             265             270
Gln Ile Gln Pro Asp Leu His Thr Asn Asp Glu Cys Val Ala Thr Tyr
            275             280             285
Lys Gly Val Pro Phe Glu Val Lys Gly Lys Gly Val Cys Arg Ala Gln
    290             295             300
Thr Met Ser Asn Ser Gly Ile Lys
305             310

<210> SEQ ID NO 4
<211> LENGTH: 14
<212> TYPE: PRT
<213> ORGANISM: Artificial
<220> FEATURE:
<223> OTHER INFORMATION: Synthetic peptide

<400> SEQUENCE: 4

Cys Asp Ala Phe Pro Gly Glu Pro Asp Lys Glu Leu Asn Pro
1               5                   10
```

METHODS AND PHARMACEUTICAL FORMULATIONS FOR THE TREATMENT OF PULMONARY HYPERTENSION

RELATED APPLICATION INFORMATION

This application is a continuation application of co-pending U.S. patent application Ser. No. 09/738,685, filed on Dec. 15, 2000 now abandoned, which claims the benefit of U.S. Provisional Application Ser. No. 60/177,008, filed Jan. 19, 2000 and U.S. Provisional Application Ser. No. 60/197,492, filed Apr. 17, 2000, the disclosures of which are incorporated by reference herein in their entirety.

RELATED APPLICATIONS

This application claims the benefit of U.S. Provisional Application Ser. No. 60/177,008, filed Jan. 19, 2000 and U.S. Provisional Application Ser. No. 60/197,492, filed Apr. 17, 2000, the disclosures of both of which are incorporated by reference herein in their entirety.

STATEMENT OF FEDERAL SUPPORT

This invention was made with United States Government support under Grant Number HL-60061 from the National Institutes of Health. The United States Government has certain rights to this invention.

FIELD OF THE INVENTION

This invention relates to pulmonary hypertension and compounds, formulations and methods useful in the treatment thereof.

BACKGROUND OF THE INVENTION

Pulmonary hypertension (PHTN) is a serious disorder characterized by an increase in pulmonary vascular resistance and classified clinically as either primary pulmonary hypertension or secondary pulmonary hypertension. In its most common form, pulmonary hypertension usually presents as a manifestation of an obvious or explicable increase in vascular resistance, such as obstruction to blood flow by pulmonary emboli, malfunction of the heart's valves or muscle in handling blood after its passage through the lungs, diminution in pulmonary vessel diameter as a reflex response to hypoventilation and/or low oxygenation, or a mismatch of vascular capacity and essential blood flow, such as shunting of blood in congenital abnormalities or surgical removal of lung tissue. Such pulmonary hypertension is referred to as secondary pulmonary hypertension. Secondary pulmonary hypertension may be a result of chronic obstructive or interstitial lung disease, recurrent pulmonary emboli, liver disease, or pre-existing heart disease.

Pulmonary hypertension where increased vascular resistance is without an obvious cause is classified as primary pulmonary hypertensions (PPH), and is diagnosed after the exclusion of the causes of secondary pulmonary hypertension. PPH is characterized by an undefined injury to the pulmonary vascular endothelium, resulting in an impaired ability to maintain a relaxed state of vasomotor tone, intense medial hypertrophy, intimal proliferation that compromises the vascular lumen, and a conversion within the pulmonary arterial bed to a procoagulant state that disposes the subject to the development of in situ thrombosis. See S. Rich, "Primary Pulmonary Hypertension," in *Harrison's Principles of Internal Medicine* 14th Edition (A. S. Fauci et al., eds., McGraw-Hill, New York (1998)), at p. 1466. Additionally, PPH is inexplicably associated with cirrhosis and portal hypertension. Id. Although the etiology of PPH remains unknown, risk factors linked to its development include essential hypertension, human immunodeficiency virus (HIV), anorexigens, collagen vascular disease, and congenital shunts resulting in increased pulmonary blood flow. Additionally, a genetic basis for the disorder appears to exist. Id.

Despite the diversity of possible causes of the disorder, the disease course of pulmonary hypertension is sadly predictable. Untreated pulmonary hypertension leads to progressive cor pulmonale (enlargement and strain of the right ventricle of the heart, sometimes to the point of failure). Subsequently, a pulmonary crisis characterized by decompensated right heart failure develops. The prognosis for patients with primary pulmonary hypertension is poor, with a median survival time of two to three years from diagnosis. Generally, progress of the disorder is inexorable via syncope and right heart failure, and death is often sudden.

U.S. Pat. No. 5,650,395 to Hurel describes the treatment of pulmonary hyertension by the administration of bombesin antagonists to lower pulmonary blood pressure. U.S. Pat. No. 5,153,222 to Tadepalli et al. describes the treatment of pulmonary hypertension by the administration of benzidine prostaglandins, while U.S. Pat. No. 5,028,628 to Tadepalli et al. describes the treatment of pulmonary hypertension by the administration of non-benzidine prostaglandins. U.S. Pat. No. 5,554,610 to Williams et al. describes the treatment of pulmonary hypertension and related conditions by the inhalation administration of vasodilators such as ganglion blockers, sympathetic nerve blockers and direct vasodilators.

Other known treatments for pulmonary hypertension include the administration of compounds such as calcium channel blockers (e.g., nifedipine or diltiazem), prostacycline, anticoagulants (e.g., warfarin), nitroprusside, hydralazine, nitrous oxide, L-arginine, and digoxin. Unfortunately, several of these methods are associated with serious side effects, including acute right ventricular ischemia, and complications from the catheterization required to administer some of the compounds. In severe cases of pulmonary hypertension, where the condition is refractory to the administration of drugs, lung or heart-lung transplantation is the only effective treatment available to clinicians. However, this treatment has numerous disadvantages due to its inherently invasive nature and the risk of organ rejection. Given the foregoing, a need exists for alternative and effective methods of treating pulmonary hypertension.

As set forth in U.S. Pat. No. 5,641,867 to Stern et al., endothelialmonocyte activating polypeptide II (EMAP II) is a polypeptide of approximately 20 kDa molecular weight. The polypeptide has been has been isolated and cloned, and is not a member of previously described cytokine/chemokine families. EMAP II has been shown to activate endothelial cells and mononuclear cells, potentiating their participation in procoagulant reactions through the induction of tissue factor, and to promote the migration of monocytes and polymorphonuclear leukocytes (PMNs). See A. Asher, et al., *J. Immunol.* 138, 963-974 (1987) and P. Nawroth, et al., *J. Exp. Med.* 168, 6637-647 (1988). However, the role of EMAP II in the formation of pulmonary hypertension has heretofore not been described.

SUMMARY OF THE INVENTION

The present inventor has found that the polypeptide EMAP II is highly expressed in the stroma of the thickened vasculature found in the lungs of subjects suffering from pulmonary hypertension. Although not wishing to be bound by any particular theory of the invention, the present inventors have determined that EMAP II plays a role in the formation of pulmonary hypertension.

Accordingly, a first aspect of the invention is a method of treating pulmonary hypertension in a subject in need of such treatment. The method comprises inhibiting EMAP II activity in the subject by an amount effective to treat the pulmonary hypertension. The inhibiting step may be carried out by any suitable means, such as by administering to the subject a compound that specifically binds to EMAP II in an amount effective to treat the pulmonary hypertension, by downregulating EMAP II expression in the subject by an amount effective to treat the pulmonary hypertension, or by administering an EMAP II receptor antagonist to the subject in an amount effective to treat the pulmonary hypertension.

Stated otherwise, the present invention provides a method of treating pulmonary hypertension in a subject in need of such treatment by administering to the subject an active compound that inhibits EMAP II activity in the subject by an amount effective to treat the pulmonary hypertension. Any suitable active compound may be employed, including a compound that specifically binds to EMAP II (e.g., an antibody), a compound that downregulates EMAP II expression (e.g., an antisense oligonucleotide), or an EMAP II receptor antagonist.

A second aspect of the present invention is a pharmaceutical formulation for the treatment of pulmonary hypertension comprising an active compound selected from the group consisting of compounds that specifically bind to EMAP II, compounds that inhibit the expression of EMAP II, and EMAP II receptor antagonists; and a pharmaceutically acceptable carrier.

A third aspect of the present invention is a method of screening for compounds useful for treating pulmonary hypertension in a subject in need thereof. The method comprises contacting a test compound (e.g., a protein or peptide) to a probe molecule, the probe molecule being selected from the group consisting of EMAP II and fragments thereof, and then detecting the presence or absence of binding of the test compound to the probe molecule, the presence of binding indicating that the compound may be useful for treating pulmonary hypertension.

A fourth aspect of the present invention is a method of screening for compounds useful for treating pulmonary hypertension, comprising contacting a test compound (e.g., an oligonucleotide) to a probe molecule, the probe molecule being selected from the group consisting of DNA encoding EMAP II, RNA encoding EMAP II, and fragments thereof, and then detecting the presence or absence of binding of the test compound to the probe molecule, the presence of binding indicating that the compound may be useful for treating pulmonary hypertension.

A fifth aspect of the present invention is a method of screening for compounds useful for treating pulmonary hypertension, comprising determining in vitro whether a test compound inhibits expression of EMAP II, the inhibition of expression of EMAP II indicating the compound may be useful for treating pulmonary hypertension in a subject.

A sixth aspect of the present invention is the use of an active compound as described herein for the manufacture of a medicament for the therapeutic or prophylactic treatment of pulmonary hypertension in a subject in need thereof.

The foregoing and other aspects of the present invention are explained in detail in the specification set forth below.

DETAILED DESCRIPTION OF THE PREFERRED EMBODIMENTS

The present invention will now be described more fully hereinafter, in which preferred embodiments of the invention are described. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

As used herein, the term "pulmonary hypertension" encompasses arterial hypertension, capillary hypertension and vaso-hypertension, and includes both primary and secondary pulmonary hypertension, as these terms are ordinarily understood by clinicians. Subjects suffering from primary pulmonary hypertension may or may not be suffering with the attendant disorders known as pulmonary venoocclusive disease and pulmonary capillary hemangiomatosis. Generally, subjects suffering with primary pulmonary hypertension will exhibit the pathological indicia set forth above (e.g., an undefined injury to the pulmonary vascular endothelium resulting in an impaired ability to maintain a relaxed state of vasomotor tone, intense medial hypertrophy, etc.).

As used herein, the term "secondary pulmonary hypertension" includes but is not limited to pulmonary hypertension occurring secondary to pulmonary diseases such as chronic bronchitis, emphysema, chronic obstructive pulmonary disorder, kyphoscoliosis, and the like. Furthermore, secondary pulmonary hypertension, as used herein, encompasses pulmonary hypertension secondarily associated with hepatic cirrhosis, cor pulmonale, right heart failure, and congenital abnormalities of the heart such as atrial septal defect, tetralogy of Fallot, ventricular septal defect and persistent ductus arteriosus.

Subjects suffering with pulmonary hypertension will generally but not necessarily exhibit plexogenic pulmonary hypertension, a histological condition identified by the presence of plexiform lesions, concentric luminal proliferation, and fibrinoid necrosis within the pulmonary vasculature. These lesions are characteristic of both primary pulmonary hypertension and secondary pulmonary hypertension. Other vascular indications of pulmonary hypertension may or may not be present in subjects suffering with pulmonary hypertension, and when present may include thrombotic arteriopathy such as eccentric intimal fibrosis with medial hypertrophy, fibro-elastic intimal pads in the arteries and arterioles of the pulmonary vasculature, and evidence of old recanalized thrombi appearing as fibrous webs. See Rich, supra, at p. 1466.

While subjects treated by the present invention are primarily and preferably human subjects, the invention may also be carried out in animal subjects, particularly mammalian subjects such as mice, rats, dogs, cats, livestock and horses for veterinary purposes, and for drug screening and drug development purposes. Human subjects include newborn, juvenile, adolescent and adult humans.

Subjects that may be treated by the methods of the present invention include those suffering from pulmonary hypertension, and those at risk for developing pulmonary hypertension. At-risk individuals include, but are not limited to, individuals with a family history of pulmonary hypertension, individuals who have previously been treated for disorders that are associated with secondary pulmonary hypertension as described herein, and individuals presenting any other clinical indicia suggesting that they have an increased likelihood of developing pulmonary hypertension. Alternatively stated, an at-risk individual is any individual who is believed to be at a higher risk than the general population for developing pulmonary hypertension.

The terms "treating" and "treatment" as used herein refer to any type of treatment that imparts a benefit to a patient afflicted with pulmonary hypertension, including improvement in the condition of the patient (e.g., in one or more symptoms), delay in the progression of the pulmonary hypertension, etc. As used herein, "treatment" is not necessarily meant to imply cure or complete abolition of pulmonary hypertension. Alternatively stated, and as used herein, "treatment" of pulmonary hypertension refers to methods of inhibiting or slowing the progression of pulmonary hypertension, reducing the incidence of pulmonary hypertension, or preventing pulmonary hypertension. As such, the term "treatment" also includes prophylactic treatment of the subject to prevent the onset of pulmonary hypertension. By the terms "prevention of pulmonary hypertension" or "preventing pulmonary hypertension" it is intended that the inventive methods eliminate or reduce the incidence or onset of pulmonary hypertension, as compared to that which would occur in the absence of treatment. Alternatively stated, the present methods slow, delay, control, or decrease the likelihood or probability of pulmonary hypertension in the subject, as compared to that which would occur in the absence of treatment.

As used herein, an "active compound" is a compound that inhibits EMAP II activity, including compounds that specifically bind to EMAP II (e.g., an antibody), compounds that downregulate EMAP II expression (e.g., an antisense oligonucleotide), or EMAP II receptor antagonists.

As noted above, a first aspect of the invention is a method of treating pulmonary hypertension in a subject in need of such treatment. The method comprises inhibiting EMAP II activity in the lungs, and particularly in the pulmonary vasculature of a subject suffering from or at risk for developing pulmonary hypertension.

The inhibiting step may be carried out by any suitable means. For example, it may be carried out by administering a compound that specifically binds to EMAP II to the subject in an amount effective to treat pulmonary hypertension. Such compounds may be antibodies (including polyclonal and monoclonal antibodies, antibody fragments, humanized or chimeric antibodies, etc., that retain the combining region that specifically binds to EMAP II). The antibodies may be of any type of immunoglobulin, including but not limited to IgG and IgM immunoglobulins. The antibodies may be of any suitable origin, such as chicken, goat, rabbit, horse, etc., but are preferably mammalian and most preferably human. The antibody may be administered directly or through an intermediate that expresses the antibody in the subject. Examples of antibodies to EMAP II are provided in U.S. Pat. No. 5,641,867 to Stern et al. Examples of the different forms of therapeutic antibodies are given in U.S. Pat. No. 5,622,700 to Jardieu et al., the disclosure of which is incorporated herein by reference.

The inhibiting step may also be carried out by downregulating EMAP II expression in the subject by an amount effective to treat pulmonary hypertension in the lungs of the subject. Compounds useful for downregulating EMAP II expression are, in general, antisense oligonucleotides that bind to EMAP II mRNA and disrupt translation thereof, or oligonucleotides that bind to EMAP II DNA and disrupt transcription thereof. Such oligonucleotides may be natural or synthetic (such as described in U.S. Pat. No. 5,665,593 to Kole, the disclosure of which is incorporated by reference herein in its entirety), and are typically at least 4, 6 or 8 nucleotides in length, up to the full length of the corresponding DNA or mRNA. Such oligonucleotides are selected to bind to the DNA or mRNA by Watson-Crick pairing based on the known sequence of the EMAP II DNA (SEQ ID NO: 1) as described in U.S. Pat. No. 5,641,867 to Stern et al. For example, an antisense oligonucleotide of the invention may consist of a 4, 6 or 8 or more nucleotide oligonucleotide having a base sequence corresponding to the EMAP II DNA sequence (SEQ ID NO: 1) disclosed in Stern et al., supra, up to 20, 30, or 40 nucleotides in length, or even the full length of the DNA sequence. In addition, such compounds may be identified in accordance with known techniques as described below.

The inhibiting step may be carried out by administering an EMAP II receptor antagonist to the subject in an amount effective to treat pulmonary hypertension in the subject. EMAP II receptor antagonists may be identified in accordance with known techniques, but are in general analogs of EMAP II, such as EMAP II having three to five N-terminal and/or C-terminal amino acids deleted.

Active compounds that are nucleotides or proteins (e.g., antibodies) may be administered either directly as described above or through a vector intermediate that expresses the same in the subject. Thus vectors used to carry out the present invention are, in general, RNA virus or DNA virus vectors, such as lentivirus vectors, papovavirus vectors (e.g., SV40 vectors and polyoma vectors), adenovirus vectors and adeno-associated virus vectors. See generally T. Friedmann, Science 244, 1275 16 (June 1989). Examples of lentivirus vectors that may be used to carry out the present invention include Moloney Murine Leukemia Virus vectors, such as those described in U.S. Pat. No. 5,707,865 to Kohn. Any adenovirus vector can be used to carry out the present invention. See, e.g., U.S. Pat. No. 5,518,913, U.S. Pat. No. 5,670,488, U.S. Pat. No. 5,589,377; U.S. Pat. No. 5,616,326; U.S. Pat. No. 5,436,146; and U.S. Pat. No. 5,585,362. The adenovirus can be modified to alter or broaden the natural tropism thereof, as described in S. Woo, *Adenovirus redirected*, Nature Biotechnology 14, 1538 (November 1996). Any adeno-associated virus vector (or AAV vector) can also be used to carry out the present invention. See, e.g., U.S. Pat. No. 5,681,731; U.S. Pat. No. 5,677,158; U.S. Pat. No. 5,658,776; U.S. Pat. No. 5,658,776; U.S. Pat. No. 5,622,856; U.S. Pat. No. 5,604,090; U.S. Pat. No. 5,589,377; U.S. Pat. No. 5,587,308; U.S. Pat. No. 5,474,935; U.S. Pat. No. 5,436,146; U.S. Pat. No. 5,354,678; U.S. Pat. No. 5,252,479; U.S. Pat. No. 5,173,414; U.S. Pat. No. 5,139,941; and U.S. Pat. No. 4,797,368. The regulatory sequences, or the transcriptional and translational control sequences, in the vectors can be of any suitable source, so long as they effect expression of the heterologous nucleic acid encoding the desired active compound in the target cells. For example, commonly used promoters are the LacZ promoter, and promoters derived from polyoma, Adenovirus 2, and Simian virus 40 (SV40). See, e.g., U.S. Pat. No. 4,599,308. The heterologous nucleic acid may encode any product that inhibits the expression of the EMAP II gene in cells infected by the vector, such as an antisense oligonucleotide that specifically binds to the EMAP II mRNA to disrupt or inhibit translation thereof, a ribozyme that specifically binds to the EMAP II mRNA to disrupt or inhibit translation thereof, or a triplex nucleic acid that specifically binds to the EMAP II duplex DNA and disrupts or inhibits transcription thereof. All of these may be carried out in accordance with known techniques, as (for example) described in U.S. Pat. Nos. 5,650,316; 5,176,996; and 5,650,316 for triplex compounds, in U.S. Pat. Nos. 5,811,537; 5,801,154; and 5,734,039 for antisense compounds, and in U.S. Pat. Nos. 5,817,635; 5,811,300; 5,773,260; 5,766,942; 5,747,335; and 5,646,020 for ribozymes (the disclosures of which are incorporated by reference herein in their entirety). The length of the heterologous nucleic acid is not critical so long as the intended function is achieved, but the heterologous nucleic acid is typically from 5, 8, 10 or 20 nucleic acids in length up to 20, 30, 40 or 50 nucleic acids in length, up to a length equal the full length of the EMAP II gene (SEQ ID NO: 1). Once prepared, the recombinant vector can be reproduced by (a) propagating the vector in a cell culture, the cell culture comprising cells that permit the growth and reproduction of the vector therein; and then (b) collecting the recombinant vector from the cell culture, all in accordance with known techniques. The viral vectors collected from the culture may be separated from the culture medium in accordance with known techniques, and combined with a suitable pharmaceutical carrier for administration to a subject. Such pharmaceutical carriers include, but are not limited to, sterile pyrogen-free water or sterile pyrogen-free saline solution. If desired, the vectors may be packaged in liposomes for administration, in accordance with known techniques.

The dosage of the recombinant vector administered will depend upon factors such as the particular disorder, the particular vector chosen, the formulation of the vector, the condition of the patient, the route of administration, etc., and can be optimized for specific situations. In general, the dosage is from about $10^7$, $10^8$, or $10^9$ to about $10^{11}$, $10^{12}$, or $10^{13}$ plaque forming units (pfu).

In addition to their pharmaceutical or veterinary use, the recombinant vectors of the present invention (also encompassed by the term "active compounds" as used herein) are useful in vitro to distinguish cells in culture based on their response to other active compounds, to induce apoptosis, etc. Such techniques are useful for both carrying out cell culture procedures and for drug screening purposes.

The active compounds of the present invention can be administered either before or during pulmonary crises. Further, they can also be administered prior to single-lung, double-lung, or heart-lung transplant. In addition, it may be desirable to give the active compound to the subject over a long period as an adjunct to, e.g., the standard therapies for heart failure as a result of pulmonary hypertension, or therapies associated with any other disorder clinically associated with pulmonary hypertension.

Active compounds of the present invention may be administered either alone or optionally in conjunction with other compounds useful in the treatment of pulmonary hypertension. Examples of such agents, referred to herein as "supplemental compounds," include, but are not limited to, vasodilators (e.g., adenosine, β-adrenergic agonists or antagonists, β-adrenergic blockers, α-adrenergic blockers, diuretics, smooth muscle vasodilators, nitrates, and angiotensin-converting enzyme inhibitors), calcium channel blockers (e.g., nifedipine or diltiazem), prostacycline, anticoagulants (e.g., warfarin), nitroprusside, hydralazine, nitrous oxide, L-arginine, and digoxin.

The co-administration of supplemental compounds can be performed before, after, or during the administration of the active compound. The supplemental compounds may optionally be administered concurrently. As used herein, the word "concurrently" means sufficiently close in time to produce a combined effect (that is, concurrently may be simultaneously, or it may be two or more events occurring within a short time period before or after each other). Simultaneous administration may be carried out by mixing the compounds prior to administration, or by administering the compounds at the same point in time but at different anatomic sites or using different routes of administration.

Active and supplemental compounds useful for effecting methods of the invention may be administered by any suitable means, including by oral, rectal, topical, buccal, parenteral, intramuscular, intradermal, intravenous, transdermal, intraperitoneal, subcutaneous, intraarterial, intravenous, intralesional and intrathecal administration. When administered by injection, the injection may be through a syringe, through a canula or catheter into a desired vessel or organ, etc. The compounds may also and preferably are administered directly into the lungs of the subject, such as by the inhalation of respirable aerosol particles comprising the active compound.

Pharmaceutical formulations of the invention typically comprise an active compound selected from the group consisting of compounds that specifically bind to EMAP II (e.g., an antibody as described above), compounds that inhibit the expression of EMAP II, and EMAP II receptor antagonists, and a pharmaceutically acceptable carrier. The term "pharmaceutically acceptable" as used herein means that the carrier is suitable for administration to a subject to achieve the treatments described herein, is compatible with any other ingredients in the formulation, and is not unduly deleterious to the patient in light of the severity of the disease and necessity of the treatment. Any pharmaceutically acceptable carrier may be employed in the present invention, such as sterile saline solution, sterile water, etc. The pharmaceutical formulation may optionally contain more than one active compound as described herein, or one or more supplemental compounds as described herein.

The active compounds described herein may be formulated for administration in a pharmaceutical carrier in accordance with known techniques. See, e.g., *Remington, The Science And Practice of Pharmacy 9th Ed*. (A. R. Gennaro, ed., Mack Publishing Co., Easton, Pa., 1995). In the manufacture of a pharmaceutical formulation according to the invention, the active compound (including the physiologically acceptable salts thereof) is typically admixed with, inter alia, the pharmaceutically acceptable carrier. The carrier may be a solid or a liquid, or both, and is preferably formulated with the compound as a unit-dose formulation, for example, a tablet, which may contain from 0.01 or 0.5% to 95% or 99% by weight of the active compound.

The pharmaceutical formulation may optionally include one or more accessory ingredients. Thus, in addition to active and/or supplemental compounds of the present invention, the pharmaceutical formulation may contain additives such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use.

The formulations of the invention include those suitable for oral, rectal, topical, buccal (e.g., sub-lingual), vaginal, parenteral (e.g., subcutaneous, intraperitoneal, intramuscular, intradermal, intraarticular, intrathecal, intralesion or intravenous), topical (i.e., both skin and mucosal surfaces, including airway surfaces), inhalation and transdermal administration, although the most suitable route in any given case will depend on the nature and severity of the condition being treated and on the nature of the particular active compound which is being used. In the practice of the present invention, preferred routes of administration include intravenous, intraperitoneal, and inhalation administration.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound in a unit dosage form in a sealed container. The compound is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound. When the compound is substantially water-insoluble, a sufficient amount of emulsifying agent which is physiologically acceptable may be employed in sufficient quantity to emulsify the compound or salt in an aqueous carrier. Useful emulsifying agents include but are not limited to phosphatidyl choline and lecithin.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3, 318 (1986)) and typically take the form of an optionally buffered aqueous solution of the active compound. Suitable formulations comprise citrate or bistris buffer (pH 6) or ethanol/water and contain from 0.1 to 0.2M active ingredient.

Formulations suitable for rectal administration are preferably presented as unit dose suppositories. These may be prepared by admixing the active compound with one or more conventional solid carriers, for example, cocoa butter, and then shaping the resulting mixture. Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof. Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Optionally, the present invention provides liposomal formulations of the compounds disclosed herein and salts thereof. The technology for forming liposomal suspensions is well known in the art. When the active compound is aqueous-soluble, using conventional liposome technology the same may be incorporated into lipid vesicles. In such an instance, due to the water solubility of the compound, the compound will be substantially entrained within the hydrophilic center or core of the liposomes. The lipid layer employed may be of any conventional composition and may either contain cholesterol or may be cholesterol-free. When the active compound is water-insoluble, again employing conventional liposome formation technology, the compound may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the active compounds disclosed herein may be lyophilized to produce a lyophilizate which may be reconstituted with a pharmaceutically acceptable carrier, such as water, to regenerate a liposomal suspension.

In one embodiment of the invention, the active compounds or pharmaceutical formulations of the invention are administered directly to the lungs of the subject by any suitable means, but are preferably administered by administering an aerosol suspension of respirable particles comprised of the active compound, which the subject inhales. The active compound can be aerosolized in a variety of forms, such as, but not limited to, dry powder inhalants, metered dose inhalants, or liquid/liquid suspensions. The respirable particles may be liquid or solid.

Solid or liquid particulate forms of the active compound prepared for practicing the present invention should include particles of respirable size: that is, particles of a size sufficiently small to pass through the mouth and larynx upon inhalation and into the bronchi and alveoli of the lungs. In general, particles ranging from about 1 to 10 microns in size are within the respirable range. Particles of non-respirable size which are included in the aerosol tend to be deposited in the throat and swallowed, and the quantity of non-respirable particles in the aerosol is preferably minimized. The particulate pharmaceutical composition may optionally be combined with a carrier to aid in dispersion or transport. A suitable carrier such as a sugar (i.e., lactose, sucrose, trehalose, mannitol) may be blended with the active compound or compounds in any suitable ratio (e.g., a 1 to 1 ratio by weight).

Aerosols of liquid particles comprising the active compound may be produced by any suitable means, such as with a pressure-driven aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic but may be hypertonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 200 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for-example, ethanol, surfactants, such as oleic acid or sorbitan trioleate, antioxidants and suitable flavoring agents.

Any propellant may be used in carrying out the present invention, including both chlorofluorocarbon-containing propellants and non-chlorofluorocarbon-containing propellants. Thus, fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3$—CHF—$CF_2$H; $CF_3$—$CH_2$—$CF_2$H; $CF_3$—CHF—$CF_3$; $CF_3$—$CH_2$—$CF_3$; $CF_3$—CHCl—$CF_2$Cl; $CF_3$—CHCl—$CF_3$; cy-C($CF_2$)$_3$—CHCl; $CF_3$—CHCl—$CH_2$Cl; $CF_3$—CHF—$CF_2$Cl; $CF_3$—CHCl—CFHCl; $CF_3$—CFCl—CFHCl; $CF_3$—$CF_2$—$CF_2$H; $CF_3$—$CF_2$—$CH_3$; $CF_2$H—$CF_2$—$CFH_2$; $CF_3$—$CF_2$—$CFH_2$; $CF_3$—$CF_2$—$CH_2$Cl; $CF_2$H—$CF_2$—$CH_3$; $CF_2$H—$CF_2$—$CH_2$Cl; $CF_3$—$CF_2$—$CF_2$—$CH_3$; $CF_3$—$CF_2$—$CF_2$—$CF_2$H; $CF_3$—CHF—CHF—$CF_3$; $CF_3$—O—$CF_3$; $CF_3$—O—$CF_2$H; $CF_2$H—H—O—$CF_2$H; $CF_2$H—O—$CFH_2$; $CF_3$—O—$CH_3$; $CF_3$—O—$CF_2$—$CF_2$H; $CF_3$—O—$CF_2$—O—$CF_3$; cy-$CF_2$—$CF_2$—O—$CF_2$—; cy-CHF—$CF_2$—O—$CF_2$—; cy-$CH_2$—$CF_2$—O—$CF_2$—; cy-$CF_2$—O—$CF_2$—O—$CF_2$—; $CF_3$—O—$CF_2$—Br; $CF_2$H—O—$CF_2$—Br; and mixtures thereof, where "cy" denotes a cyclic compound in which the end terminal covalent bonds of the structures shown are the same so that the end terminal groups are covalently bonded together. Particularly preferred are hydrofluoroalkanes such as 1,1,1,2-tetrafluoroethane and heptafluoropropane. A stabilizer such as a fluoropolymer may optionally be included in formulations of fluorocarbon propellants, such as described in U.S. Pat. No. 5,376,359 to Johnson.

Compositions containing respirable dry particles of micronized active compound of the present invention may be prepared by grinding the dry active compound with, e.g., a mortar and pestle or other appropriate grinding device, and then passing the micronized composition through a 400 mesh screen to break up or separate out large agglomerates.

The aerosol, whether formed from solid or liquid particles, may be produced by the aerosol generator at a rate of from about 10 to 150 liters per minute. Aerosols containing greater amounts of medicament may be administered more rapidly. Typically, each aerosol may be delivered to the patient for a period from about 30 seconds to about 20 minutes, with a delivery period of about five to ten minutes being preferred.

Regardless of the route of administration of the active compounds or formulations of the invention, the therapeutically effective dosage of any one active compound, the use of which is in the scope of present invention, will vary somewhat from compound to compound, and patient to patient, and will depend upon factors such as the age, weight and condition of the patient, and the route of delivery. Such dosages can be determined in accordance with routine pharmacological procedures known to those skilled in the art. For example, as a general proposition, a dosage from about 0.1 to about 50 mg/kg will have therapeutic efficacy, with all weights being calculated based upon the weight of the active compound. Toxicity concerns at the higher level may restrict intravenous dosages to a lower level such as up to about 10 mg/kg. A dosage from about 10 mg/kg to about 50 mg/kg may be employed for oral administration. Typically, a dosage from about 0.5 mg/kg to 5 mg/kg may be employed for intramuscular injection. Preferred dosages are 1 μmol/kg to 50 μmol/kg, and more preferably 22 μmol/kg and 33 μmol/kg of the compound for intravenous or oral administration.

To further exemplify estimated dosages of the compounds of the present invention, for antisense oligonucleotides the dosage is preferably one which produces intracellular concentrations of the oligonucleotide of from 0.05 to 50 μM. Typically the dosage to a human will be from about 0.01, 0.1 or 1 mg/Kg up to 50, 100, or 150 mg/Kg. In an additional example, for antibodies the dosage is typically 0.01, 0.05 or 0.1 mg/Kg up to 20, 40 or 60 mg/Kg.

When administration of the active compounds or pharmaceutical formulations is via inhalation, the dosage of active compound will also vary depending on the condition being treated and the state of the subject, but generally may be an amount sufficient to achieve dissolved concentrations of active compound on the airway surfaces of the subject of from about $10^{-9}$ to about $10^{-1}$ Moles/liter, and more preferably from about $10^{-6}$ to about $10^{-4}$ Moles/liter.

Depending upon the solubility of the particular formulation of active compound administered to a subject, the daily dose may be divided among one or several unit dose administrations. The daily dose by weight will depend upon the age and condition of the subject. Such a daily dose may be as low as 1 mg per day, under certain circumstances may be as low as 0.5 mg per day, and may even be as low as 0.1 mg/day. The daily dose of the active compounds may also be as high as 200 mg/day, under certain conditions may be as high as 500 mg/day, and may even be as high as 1000 mg/day. The doses of the active compounds may be provided as one or several prepackaged units. The duration of the treatment is usually once per day for a period of time that will vary by subject, but will generally last until the condition is essentially controlled. Lower doses given less frequently can be used prophylactically to prevent or reduce the incidence of recurrence of the pulmonary hypertension.

In vitro methods of screening compounds for efficacy in carrying out the methods of treatment described above are also an aspect of the present invention. In general, in one embodiment, such methods comprise determining in vitro whether the compound inhibits the expression of EMAP II (preferably the mammalian gene, and most preferably the human gene). The inhibition of expression of EMAP II indicates the compound is useful in the methods of treatment described above. Numerous such screening methods are available. The methods can be carried out in a cell or cells, or can be carried out in essentially cell free preparation. The method can be carried out by screening for compounds that specifically disrupt either transcription or translation of EMAP II. The compound to be screened may be a member of a library of compounds (the term "compound" as used in this respect referring to both small organic compounds and other therapeutic agents such as recombinant viral vectors). The method may be carried out as a single assay, or may be implemented in the form of a high throughput screen in accordance with a variety of known techniques.

In another embodiment of the invention, the method of screening compounds comprises determining in vitro whether the compound specifically binds to EMAP II (including fragments thereof) (preferably the mammalian gene product; most preferably the human gene product). The determining step can be carried out by screening for binding of a test compound or probe molecule to the entire full length EMAP II gene product (SEQ ID NO: 2 or 3), or to a peptide fragment thereof (e.g., a fragment of from 5, or 10 amino acids in length up to the full length of EMAP II). The binding of the compound to the EMAP II indicates that the compound is useful in the methods of treatment described herein. Such techniques can be carried out by contacting a probe compound to EMAP II or a fragment thereof in any of the variety of known combinatorial chemistry techniques (including but not limited to split pool techniques, chip-based techniques and pin-based techniques). Any suitable solid support can be used to immobilize the EMAP II or a fragment thereof to find specific binding partners thereto (or immobilize the members of the library against which the EMAP II or fragment thereof is contacted to find specific binding partners thereto), and numerous different solid supports are well known to those skilled in the art. Examples of suitable materials from which the solid support may be formed include cellulose, pore-glass, silica gel, polystyrene, particularly polystyrene cross-linked with divinylbenzene, grafted copolymers such as polyethyleneglycol/polystyrene, polyacrylamide, latex, dimethylacrylamide, particularly cross-linked with N,N'bis-acrylolyl ethylene diamine and comprising N-t-butoxycarbonyl-beta-alanyl-N'acrylolyl hexamethylene diamine, composites such as glass coated with a hydrophobic polymer such as cross-linked polystyrene or a fluorinated ethylene polymer to which is grafted linear polystyrene, and the like. Thus the term "solid support" includes materials conventionally considered to be semi-solid supports. General reviews of useful solid supports that include a covalently-linked reactive functionality may be found in Atherton et al., *Prospectives in Peptide Chemistry,* 101-117 (1981); Amamath et al., *Chem. Rev.* 77, 183 (1977); and Fridkin, *The Peptides, Vol.* 2, (Academic Press, Inc., Chapter 3, pp. 333-363 (1979)). The solid support may take any suitable form, such as a bead or microparticle, a tube, a plate, a microtiter plate well, a glass microscope cover slip, etc.

The present invention can be used with probe molecules, or libraries (where groups of different probe molecules are employed), of any type. In general, such probe molecules are organic compounds, including but not limited to that may be used to carry out the present include oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, catalysts, as well as combinations thereof. Oligomers include peptides (e.g., oligopeptides) and proteins, oligonucleotides of DNA and RNA, oligosaccharides, polylipids, polyesters, polyamides, polyurethanes, polyureas, polyethers, polyphosphorus derivatives such as phosphates, phosphonates, phosphoramides, phosphonamides, phosphites, phosphinamides, and polysulfur derivatives such as sulfones, sulfonates, sulfites, sulfonamides, sulfenamides. Numerous methods of synthesizing or applying such probe molecules on solid supports (where the probe molecule may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of which patents are incorporated herein by reference in their entirety).

Test compounds used to carry out the present invention may be of any type, including both oligomers or non-oligomers of the types described above in connection with probe molecules above. Again, such test compounds are known and can be prepared in accordance with known techniques.

Where multiple different probe molecules are desired to be tested, a screening substrate useful for the high throughput screening of molecular interactions, such as in "chip-based" and "pin-based" combinatorial chemistry techniques, can be prepared in accordance with known techniques. All can be prepared in accordance with known techniques. See, e.g., U.S. Pat. No. 5,445,934 to Fodor et al., U.S. Pat. No. 5,288,514 to Ellman, and U.S. Pat. No. 5,624,711 to Sundberg et al.

In the alternative, screening of libraries of probe molecules may be carried out with mixtures of solid supports as used in "split-pool" combinatorial chemistry techniques. Such mixtures can be prepared in accordance with procedures known in the art, and tag components can be added to the discreet solid supports in accordance with procedures known in the art. See, e.g., U.S. Pat. No. 5,565,324 to Still et al.

The present invention is explained in greater detail in the following non-limiting Examples.

EXAMPLE 1

Generation of an EMAP II Monoclonal Antibody and rEMAP II Protein Purification Synthesis of recombinant (r) EMAP II from *Escherichia coli*. The cDNA of mature human EMAP II was cloned from RT-PCR products of U937 cells' total RNA based on primers obtained from Genebank (accession no. 10119) into a TA vector obtained from Invitrogen. Confirmation of the clones was provided by sequence analysis, after which the cDNA was inserted into PET28a, a 6×his-tag containing plasmid. *E. coli* (DE3) underwent transformation with the EMAP II/PET28a plasmid and were induced with 1-4 mM Isopropyl Beta-D-Thiogalactopyranoside (IPTG). After 3-4 hours of induction, the cells were pelleted, lysed and the EMAP II protein was purified through the use of a Qiagen Nickel-NTA resin column, in accordance with the manufacturer's protocol, with all procedures performed at 4° C. Briefly, pelleted cells were lysed with 50 mM $NaH_2PO_4$ pH 8.0, 300 mM NaCl, and 10 mM imidazole in the presence of 1 mg/ml lysozyme. Following sonication, cellular debris are removed by centrifugation prior to being loaded on the Nickel-NTA resin. Following washing of the column, rEMAP II is eluted off with 8M urea, 0.1 M $NaH_2PO_4$, and 0.01 M Tris.Cl pH 5.9. Purified rEMAP II is dialyzed at 4° C. against PBS three times prior to being aliquoted and frozen at −80° C. When an aliquot of rEMAP II was thawed, it was used immediately for experiments (it was not refrozen and used in future studies).

Synthesis of antibody. The antibody is generated from the following peptide sequence:

(C)DAFPGEPDKELNP (#252-264) (SEQ ID NO: 4)

(C) is a cysteine that is assigned for use in the single point, site-directed conjugation procedure described below, and is not part of the original EMAP II antibody.

The peptide is conjugated to KLH (keyhole limpet hemacyanin) by a single point, site-directed conjugation via the terminal cysteine, in accordance with standard techniques.

For generation of the polyclonal antibody, rabbits are injected with 0.5 mg of the peptide-KLH conjugate emulsified in complete Freund's adjuvant, and subsequent injections in incomplete Freund's adjuvant, at three week intervals for a total of three to four injections. Monoclonal antibodies to EMAP II are then generated in accordance with standard techniques.

The foregoing is illustrative of the present invention and is not to be construed as limiting thereof. The invention is defined by the following claims, with equivalents of the claims to be included therein.

That which is claimed is:

1. A pharmaceutical formulation useful for treating pulmonary hypertension comprising:
   a mammalian antibody that specifically binds to endothelial-monocyte activating polypeptide II (EMAP II) of SEQ ID NO: 2 or 3; and
   a supplemental compound selected from the group consisting of a vasodilator, a calcium channel blocker, an anticoagulant, prostacycline, nitroprusside, hydralazine, nitrous oxide, L-arginine, and digoxin.

2. The pharmaceutical formulation according to claim 1, wherein the supplemental compound is a vasodilator selected from the group consisting of adenosine, a β-adrenergic agonist, a β-adrenergic antagonist, an α-adrenergic blocker, a diuretic, a smooth muscle vasodilator, nitrate, and an angiotensin-converting enzyme inhibitor.

3. The pharmaceutical formulation according to claim 1, wherein the supplemental compound is a calcium channel blocker selected from the group consisting of nifedipine and diltiazem.

4. The pharmaceutical formulation of claim 1, wherein the mammalian antibody is a human antibody.

5. The pharmaceutical formulation of claim 1, wherein the mammalian antibody is a humanized antibody.

* * * * *